United States Patent [19]

Kajioka et al.

[11] 4,398,943
[45] Aug. 16, 1983

[54] TRIAZOLINONE DERIVATIVE AND HERBICIDAL USE THEREOF

[75] Inventors: Mitsuru Kajioka, Sakai; Katsumasa Okawa, Kawachinagano; Kuniaki Taninaka, Neyagawa, all of Japan

[73] Assignee: Nikon Nohyaku Co., Ltd., Tokyo, Japan

[21] Appl. No.: 331,064

[22] Filed: Dec. 15, 1981

[30] Foreign Application Priority Data

Dec. 25, 1980 [JP] Japan ................................ 55-184557
Dec. 25, 1980 [JP] Japan ................................ 55-184558
Apr. 30, 1981 [JP] Japan ................................ 56-65497

[51] Int. Cl.³ .................... A01N 43/64; C07D 249/12
[52] U.S. Cl. .......................................... 71/92; 548/263; 548/265
[58] Field of Search .................... 548/263, 265; 71/92

[56] References Cited

U.S. PATENT DOCUMENTS 4,276,420  6/1981  Ziman ...................................... 71/92
4,318,731  3/1982  Kajioka et al. .......................... 71/92

FOREIGN PATENT DOCUMENTS 2725148  12/1978  Fed. Rep. of Germany .
2056971   3/1981  United Kingdom .

Primary Examiner—Alton D. Rollins
Attorney, Agent, or Firm—Cushman, Darby & Cushman

[57] ABSTRACT

There is provided a new herbicidal compound of the formula,

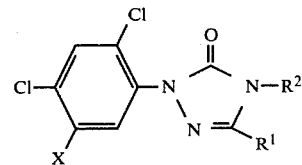

wherein $R^1$ is an alkyl group; $R^2$ is an alkynyl group, a halomethyl group, or a haloethyl group; and X is an alkoxy group, an alkenyloxy group, an alkoxy-alkoxy group, an alkynyloxy group, a hydroxy group, a halomethyloxy group, or a haloethyloxy group.

38 Claims, No Drawings

TRIAZOLINONE DERIVATIVE AND HERBICIDAL USE THEREOF

The present invention relates to a $\Delta^2$-1,2,4-triazolin-5-one derivative, usage thereof, and a process for producing it, which derivative is represented by the formula (I)

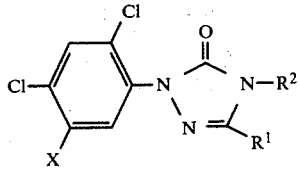

wherein $R^1$ is a $C_1$–$C_4$ alkyl group; $R^2$ is a $C_3$–$C_5$ alkynyl group, a halomethyl group, or a haloethyl group; and X is a $C_1$–$C_4$ alkoxy group, an alkenyloxy group, a $C_2$–$C_6$ alkoxyalkoxy group, an alkynyloxy group, a hydroxy group, a halomethyloxy group, or a haloethyloxy group.

The compound represented by the above formula (I) is especially useful as herbicide.

In the above formula (I), the $C_1$–$C_4$ alkyl group of $R^1$ includes methyl, ethyl, n-propyl, isopropyl, n-butyl, isobutyl, tert.-butyl and sec.-butyl groups.

The $C_3$–$C_5$ alkynyl group of $R^2$ includes, for example, propargyl, 2-methyl-3-butyn-2-yl, 2-butynyl, 3-butyn-2-yl, 1-pentyn-3-yl, 3-butynyl, 3-pentynyl, and 4-pentyn-2-yl groups.

The halomethyl group represented by $R^2$ or as a moiety of halomethyloxy represented by X include, for example, trifluoromethyl, difluoromethyl, difluorobromomethyl, and difluoro-chloromethyl groups.

The $C_1$–$C_4$ alkoxy group represented by X includes methoxy, ethoxy, n-propoxy, isopropoxy, n-butoxy, isobutoxy, tert.-butoxy, and sec.-butoxy.

The alkenyloxy group of X includes, for example, allyloxy, 3-buten-2-yloxy, 2-methyl-3-buten-2-yloxy, 3-penten-2-yloxy, 2-methyl-2-propenoxy, 2-butenoxy, 3-methyl-2-butenoxy, 3-methyl-3-butenoxy, and 1-methyl-3-butenoxy. X can also be 3-chloro-2-propenoxy.

The alkynloxy group represented by X includes, for example, propargyloxy, 2-methyl-3-butyn-2-yloxy, 2-butynoxy, 3-butyn-2-yloxy, 1-pentyn-3-yloxy, 3-butynoxy, 4-pentyn-2-yloxy and 4-hexyn-2-yloxy. X can also be 1-ethynyl-1-cyclohexyloxy.

The $C_2$–$C_6$ alkoxyalkoxy group of X includes, for example, methoxymethoxy, 2-methoxyethoxy, 2-ethoxy-ethoxy, 2-propoxyethoxy and 2-butoxyethoxy.

In the above formula (I), the compound having a halomethyl group, especially a difluoromethyl group for $R^2$, has high herbicidal activity, and low phytotoxicity against crops. Accordingly, the compound is useful as herbicide in pre- and post-emergency.

More particularly, compounds of the formula (I), wherein $R^2$ is a halomethyl group, more preferably a difluoromethyl group; and X is a $C_1$–$C_4$ alkoxy group, a $C_2$–$C_6$ alkenyloxy group, a $C_2$–$C_6$ alkoxyalkoxy group, or a $C_3$–$C_8$ alkynyloxy group, are especially useful as herbicides.

The compounds represented by the above formula (I) are novel and not reported in literatures.

As example of typical process for synthesis thereof, the following processes A and B are given.

The reaction paths are schematically shown below:

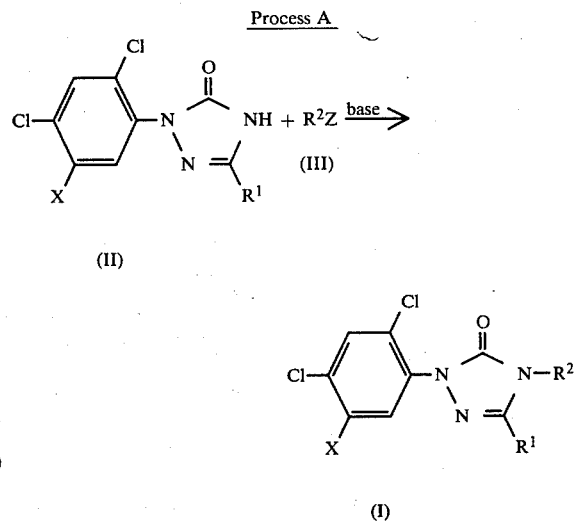

wherein, $R^1$, $R^2$ and X are the same as defined above, and Z is a halogen atom, and also the $R^2Z$ may be a haloethylene. Thus, the compound of (I) can be obtained by reacting a compound of (II) with a compound of (III) in the presence of a base.

In the process an inert solvent is preferable used. As the inert solvent, any solvent not seriously disturbing this type of reaction may be used; for example it is possible to use aromatic hydrocarbons such as benzene, toluene, chlorobenzene, and xylene; ethers such as ethyl ether, tetrahydrofuran, and dioxane; alcohols such as methanol, ethanol, propanol, and ethyleneglycol; ketones such as acetone, methyl ethyl ketone, and cyclohexanone; lower fatty acid esters such as ethyl acetate; lower fatty acid amides such as dimethylformamide and dimethylacetamide; water; and dimethylsulfoxide. These solvents may be used each alone or in combination with one another.

The bases which can be used for the above reaction include inorganic bases such as, for example, sodium carbonate, potassium carbonate, sodium hydrogencarbonate, potassium hydrogencarbonate, caustic soda, caustic potash, and alkali metal alcoholates; and organic bases such as, for example, pyridine, trimethylamine, triethylamine, diethylaniline, and 1,8-diazabicyclo-[5,4,0]-7-undecene. Particularly caustic soda, caustic potash, potassium carbonate or alkali metal alcoholates is desirable.

In case of reacting a compound of (III) with a compound of (II) a two-phase reaction can also be applied between an aqueous solution layer containing a base such as caustic soda and an organic solvent layer in the presence of a phase transfer catalyst such as triethylbenzylammonium chloride, whereby compounds of formula (I) can be synthesized in good yields.

In the step of this process, the reaction can be generally allowed to proceed under heated condition, for example, in a temperature of from 50° to 150° C. The reaction can be effected by the use of the both reactants in equimolar ratio, but it is unobjectionable to use either one in slight excess.

After the reaction has been completed, the objective material can be obtained through customary treatments of the reaction product.

Process B

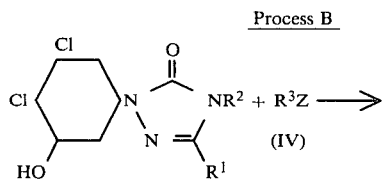
(I)a

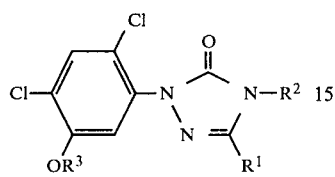
(I)b wherein, $R^1$, $R^2$ and Z are the same as defined above and Z may be a hydroxy group; $R^3$ is a $C_1$–$C_4$ alkyl group, an alkenyl group, a $C_2$–$C_6$ alkoxyalkyl group, an alkynyl group, a halomethyl group, or a haloethyl group and the $R^3Z$ may be a haloethylene.

That is, the objective compound (I)b which is one of the compounds of formula (I) can be obtained by reacting a compound of (I)a with a compound of (IV) in an inert solvent.

As the inert solvent for this reaction, those enumerated in process A can be used. In the reaction of this process, the reaction temperature used is in the range of from room temperature to 180° C.

The reaction can be effected by using reactants in equimolar ratio, but it is unobjectionable to use either one in slight excess.

After the reaction has been completed, the objective material can be obtained through customary treatments of the reaction product. For example, it is accomplished by extracting the objective material from the reaction product with a suitable solvent, washing and drying the extract, and removing the solvent.

The compound (I)a which is also one included in formula (I), can be obtained by reacting a compound of the following formula (I)c with a dealkylating agent in an inert solvent.

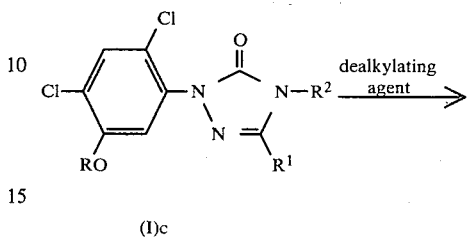
(I)c

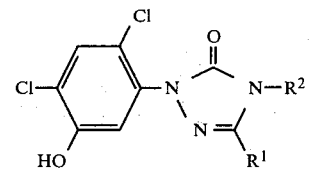
(I)a

As examples of the dealkylating agent used in this process, may be cited hydrobromic acid, hydriodic acid, thioalkoxide, trimethylsilyl iodide, and boron trichloride, but the dealkylating agent is not limited to these compounds and may be any reagent that causes this type of dealkylation.

The reaction conditions such as the kind of the inert solvent, the reaction temperature and molar ratio of the reactants used are same as the above process for obtaining the compound (I)b, and the objective compounds (I)a is recovered in the same way.

Typical example of the compounds represented by formula (I) are shown in Table 1.

TABLE 1

| Compound No. | X | $R^1$ | $R^2$ | Melting point (°C.) or refractive index |
|---|---|---|---|---|
| 1 | CH≡CCH$_2$O | CH$_3$ | CH≡CCH$_3$ | m.p. 140.6 |
| 2 | i-C$_3$H$_7$O | CH$_3$ | CH≡CCH$_2$ | $n_D^{25}$ 1.5589 |
| 3 | CH$_3$OCH$_2$O | CH$_3$ | CH≡CCH$_2$ | $n_D^{25}$ 1.5527 |
| 4 | CH$_2$=CHCH$_2$O | i-C$_3$H$_7$ | CH≡CCH$_2$ | m.p. 109.0 |
| 5 | i-C$_3$H$_7$O | CH$_3$ | CHF$_2$ | m.p. 81.3 |
| 6 | CH$_3$OCH$_2$O | CH$_3$ | CHF$_2$ | m.p. 116.4 |
| 7 | CH$_2$=CHCH$_2$O | CH$_3$ | CHF$_2$ | m.p. 96.4 |
| 8 | CH$_2$=CHCH$_2$O | i-C$_3$H$_7$ | CHF$_2$ | m.p. 93.5 |
| 9 | i-C$_3$H$_7$O | i-C$_3$H$_7$ | CHF$_2$ | m.p. 79.0 |
| 10 | CH$_3$OCH$_2$O | i-C$_3$H$_7$ | CHF$_2$ | $n_D^{18}$ 1.5312 |
| 11 | CH$_3$O | CH$_3$ | CHF$_2$ | m.p. 154.5 |
| 12 | OH | CH$_3$ | CHF$_2$ | m.p. 175.3 |
| 13 | CHF$_2$O | CH$_3$ | CHF$_2$ | m.p. 82.4° C. |
| 14 | CH≡CCH$_2$O | CH$_3$ | CHF$_2$ | m.p. 114.4° C. |
| 15 | CH≡CCH$_2$O | i-C$_3$H$_7$ | CHF$_2$ | m.p. 91.2° C. |
| 16 | CHF$_2$CF$_2$O | CH$_3$ | CHF$_2$ | $n_D^{15.0}$ 1.5013 |
| 17 | CHFClCF$_2$O | CH$_3$ | CHF$_2$ | m.p. 79-81° C. |
| 18 | i-C$_3$H$_7$O | CH$_3$ | CHF$_2$CF$_2$ | m.p. 102-103.5° C. |
| 19 | CH$_2$=CHCH$_2$O | CH$_3$ | CHF$_2$CF$_2$ | m.p. 81.8° C. |
| 20 | CH≡CCH$_2$O | CH$_3$ | CHF$_2$CF$_2$ | m.p. 116-118° C. |
| 21 | CHF$_2$CF$_2$O | CH$_3$ | CHF$_2$CF$_2$ | $n_D^{15.0}$ 1.4840 |
| 22 | i-C$_3$H$_7$O | CH$_3$ | CHFClCF$_2$ | m.p. 131.5 |
| 23 | CH$_2$=CHCH$_2$O | CH$_3$ | CHFClCF$_2$ | m.p. 96.1 |
| 24 | i-C$_3$H$_7$O | CH$_3$ | CHFBrCF$_2$ | $n_D^{26.5}$ 1.5308 |
| 25 | CH$_2$=CHCHO<br>\|<br>CH$_3$ | CH$_3$ | CHF$_2$ | $n_D^{18}$ 1.5372 |

TABLE 1-continued

| Compound No. | X | R¹ | R² | Melting point (°C.) or refractive index |
|---|---|---|---|---|
| 26 | CH₃CH=CHCHO<br>\|<br>CH₃ | CH₃ | CHF₂ | $n_D^{18}$ 1.5432 |
| 27 | CH₂=CCH₂O<br>\|<br>CH₃ | CH₃ | CHF₂ | m.p. 73.5° C. |
| 28 | CH₃CH=CHCH₂O | CH₃ | CHF₂ | m.p. 116.9° C. |
| 29 | CH₃<br>  \\<br>   C=CHCH₂O<br>  /<br>CH₃ | CH₃ | CHF₂ | m.p. 74.9° C. |
| 30 | ClCH=CHCH₂O | CH₃ | CHF₂ | m.p. 133.8° C. |
| 31 | ClCH₂CH=CHO | CH₃ | CHF₂ | m.p. 138° C. |
| 32 | CH₂=CCH₂CH₂O<br>\|<br>CH₃ | CH₃ | CHF₂ | m.p. 83.5° C. |
| 33 | CH₂=CHCH₂CHO<br>\|<br>CH₃ | CH₃ | CHF₂ | m.p. 47.6° C. |
| 34 | C₂H₅     CH₂O<br>   \\   /<br>    C=C<br>   /   \\<br>  H      H | CH₃ | CHF₂ | m.p. 115.1° C. |
| 35 | C₂H₅     CH₂CH₂O<br>   \\   /<br>    C=C<br>   /   \\<br>  H      H | CH₃ | CHF₂ | m.p. 69.1° C. |
| 36 | CH₃C≡CCH₂O | CH₃ | CHF₂ | m.p. 129.5° C. |
| 37 | C₂H₅C≡CCH₂O | CH₃ | CHF₂ | m.p. 132.7° C. |
| 38 | HC≡CCHO<br>\|<br>CH₃ | CH₃ | CHF₂ | |
| 39 | HC≡CCHO<br>\|<br>C₂H₅ | CH₃ | CHF₂ | $n_D^{18}$ 1.5423 |
| 40 | HC≡CCHO<br>\|<br>C₃H₇—n | CH₃ | CHF₂ | $n_D^{18}$ 1.5323 |
| 41 | HC≡CCO<br>  /  \\<br>CH₃  CH₃ | CH₃ | CHF₂ | m.p. 118.1° C. |
| 42 | HC≡CCO<br>  /  \\<br>CH₃  C₂H₅ | CH₃ | CHF₂ | m.p. 81.5° C. |
| 43 | HC≡CCO<br>  /  \\<br>CH₃  C₄H₉—i | CH₃ | CHF₂ | $n_D^{25}$ 1.5310 |
| 44 | HC≡CCH₂CH₂O | CH₃ | CHF₂ | m.p. 118.0° C. |
| 45 | CH₂=C=CHCH₂O | CH₃ | CHF₂ | m.p. 92.0° C. |
| 46 | CH₃C≡CCH₂CH₂O | CH₃ | CHF₂ | m.p. 146.8° C. |
| 47 | C₂H₅C≡CCH₂CH₂O | CH₃ | CHF₂ | m.p. 104.5° C. |
| 48 | CH≡CCH₂CHO<br>\|<br>CH₃ | CH₃ | CHF₂ | $n_D^{18}$ 1.5442 |
| 49 | CH₃C≡CCH₂CHO<br>\|<br>CH₃ | CH₃ | CHF₂ | $n_D^{18}$ 1.5425 |

TABLE 1-continued

| Compound No. | X | R¹ | R² | Melting point (°C.) or refractive index |
|---|---|---|---|---|
| 50 | (cyclohexyl with O and C≡CH, H) | $CH_3$ | $CHF_2$ | m.p. 115.7° C. |
| 51 | $i\text{-}C_3H_7O$ | $CH_3$ | $CF_2Br$ | m.p. 119.6° C. |

Some of the compounds represented by the formula (II) are novel and unreported in literatures.

As example of typical process for synthesis thereof, the following process is given.

The reaction path is schematically shown below:

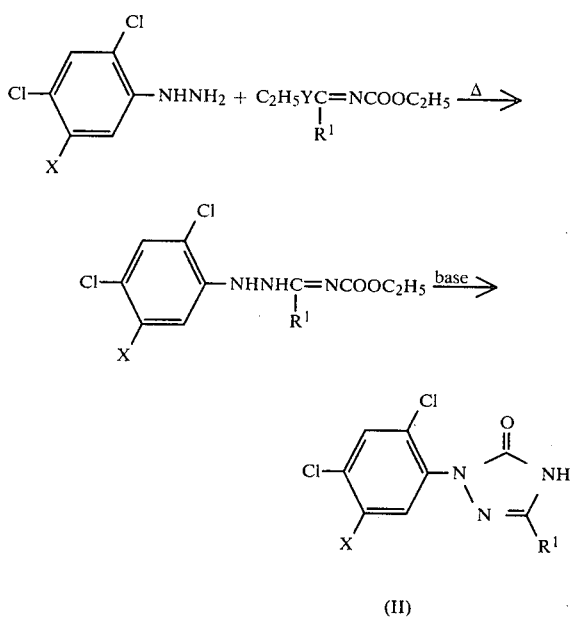

wherein, $R^1$ and X are the same as defined above, and Y is an oxygen or sulfur atom.

Typical examples of the compounds represented by formula (II) are shown in following Table.

| X | R¹ | Melting point (°C.) |
|---|---|---|
| C≡CCH₂O | $CH_3$ | 229.1 |
| CH=CCH₂O | $i\text{-}C_3H_7$ | 162.9 |
| $CH_3O$ | $CH_3$ | 240.4 |
| $CH_3O$ | $i\text{-}C_3H_7$ | 192.0 |
| $C_2H_5O$ | $CH_3$ | 226.3 |
| $C_2H_5O$ | $i\text{-}C_3H_7$ | 141.4 |
| $i\text{-}C_3H_7O$ | $CH_3$ | 165.7 |
| $i\text{-}C_3H_7O$ | $i\text{-}C_3H_7$ | 115.6 |
| $CH_2=CH-CH_2O$ | $CH_3$ | 189.3 |
| $CH_2=CH-CH_2O$ | $i\text{-}C_3H_7$ | 123.5 |
| $CH_3OCH_2O$ | $CH_3$ | 205.5 |
| OH | $CH_3$ | 275.1 |
| OH | $i\text{-}C_3H_7$ | 289.1 |

The $\Delta^2$-1,2,4-triazolin-5-one derivatives of the present invention are capable of controlling annual and perennial weeds grown in paddy fields, upland fields, orchards, and swamps, such as barnyard grass (Echinochloa Crusgalli Beauv, an annual gramineous grass which is a typical weed grown in paddy fields and strongly injurious), monochoria (Monochoria vaginalis Presl, a strongly injurious annual weed of Pontederiaceae family grown in paddy fields), umbrella plant (Cyperus difformis L., an injurious annual cyperaceous weed grown in paddy fields), slender spikerush (Eleocharis acicularis Roem. et Schult, a typical injurious perennial cyperaceous weed of paddy fields, grown also in swamps and waterways), Arrowhead (Sagittaria pygmaea Miq., an injurious perennial weed of Alismataceae family, grown in paddy fields, swamps, and ditches), bulrush (Scirpus juncoides Roxb. var. hotarui ohwi., an annual cyperaceous weed grown in paddy fields, swamps, and ditches), wild oats (Avena fatua L., an annual gramineous grass grown in plains, waste lands, and upland fields), mugwort (Artemisia princeps Pamp., a perennial composite grass grown in cultivated and uncultivated fields and mountains), large crabgrass (Digitaraia adscendcus Henr., an annual gramineous grass which is a typical strongly injurious weed grown in upland fields and orchards), Gishi-gishi (Rumex japonicus Houtt, a perennial polygonaceous weed grown in upland fields and on roadsides), umbrella sedge (Cyperus Iria L., an annual cyperaceous weed grown in upland fields and on roadsides), and Redroot pigweed (Amaranthus varidis L., an annual weed of Amaranthaceae family grown in upland fields, vacant lands, and roadsides).

Since the compounds represented by formula (I) exhibit an excellent controlling action against weeds in the prior and initial stages of emergence, their characteristic physiological activities can be manifested more effectively by treating fields with the compounds before planting useful plants therein, after planting useful plants therein (including fields such as orchards, where useful plants have already planted) but before the emergence of weeds, or after sowing of useful plants but before the emergence of the plants. However, the application mode of the present herbicides is not limited only to those described above; they can also be used as a herbicide applying at middle stage of rice for paddy fields and moreover, as a herbicide to control general weeds grown in, for example, reaped fields, temporarily noncultivated fields, ridges between paddy fields, agricultural pathways, waterways, fields constructed for pasture, graveyards, parks, roads, playgrounds, unoccupied areas around buildings, reclaimed lands, railways, and forests. Herbicidal treatment of such areas is carried out most effectively and economically but not necessarily prior to the emergence of weeds.

For applying the present compounds as a herbicide, they are generally made up, according to the customary procedure for preparing agricultural chemicals, into a form convenient to use. That is, the present compounds are blended with suitable inert carriers and, if necessary, further with adjuvants, in a suitable ratio, and through dissolution, dispersion, suspension, mechanical mixing, impregnation, adsorption, or adhesion, a suitable form of preparation, e.g., suspensions, emulsifiable concentrates, solutions, wettable powders, dusts, granules, or tablets may be obtained.

The inert carriers to be used in the formulations may be either solids or liquids. As examples of the adaptable solid carriers, may be cited vegetable powders such as soybean flour, cereal flour, wood flour, bark flour, saw dust, powdered tabaco stalk, powdered walnut shell, bran, powdered cellulose, and extraction residues of vegetables; fibrous materials such as paper, corrugated paperboard, and waste cloth; synthetic polymers such as powdered synthetic resins; inorganic or mineral products such as clays (e.g., kaolin, bentonite, and acid clay), talcs [e.g., diatomaceous earth, silica sand, mica, and "white carbon" (highly dispersed synthetic silicic acid, also called finely devided hydrated silica or hydrated silicic acid; some commercial products contain calcium silicate as major constituent)], activated carbon, powdered sulfur, pumice, calcined diatomaceous earth, ground brick, fly ash, sand, calcium carbonate, and calcium phosphate; chemical fertilizers such as ammonium sulfate, ammonium nitrate, urea, and ammonium chloride; and farmyard manure. These materials are used each alone or in combination with one another. The material usuable as liquid carriers are selected from those which are solvents for the active compounds and those which are non-solvent but can disperse the active compounds with the aid of adjuvants. For example, the following materials can be used each alone or in combination with one another: water, alcohols (e.g., methanol, ethanol, isopropanol, butanol, ethylene glycol), ketones (e.g., acetone, methyl ethyl ketone, methyl isobutyl ketone, diisobutyl ketone, and cyclohexanone), ethers (e.g., ethyl ether, dioxane, cellosolves, dipropyl ether, and tetrahydrofuran), aliphatic hydrocarbons (e.g., gasoline and mineral oils), aromatic hydrocarbons (e.g., benzene, toluene, xylene, solvent naphtha, and alkylnapthalenes), halohydrocarbons (e.g., dichloroethane, chlorinated benzenes, chloroform, and carbon tetrachloride), esters (e.g., ethyl acetate, dibutyl phthalate, diisopropyl phthalate, and dioctyl phthalate), acid amides (e.g., dimethylformamide, diethylformamide, and dimethylacetamide), nitrides (e.g., acetonitrile), and dimethyl sulfoxide.

The adjuvants, which are exemplified below, are used according to individual purposes. In some cases, they are used in combination with one another. In some other cases, no adjuvant is used at all.

For the purpose of emulsification, dispersion, solubilization and/or wetting of the active compounds, are used surface active agents, for example, polyoxy-ethylene alkylaryl ethers, polyoxyethylene alkyl ethers, polyoxyethylene higher fatty acid esters, polyoxyethylene resinates, polyoxyethylene sorbitan monolaurate, polyoxyethylene sorbitan mono-oleate, alkylarylsulfonates, naphthalenesulfonic acid condensation products, ligninsulfonates, and higher alcohol sulfate esters.

For the purpose of stabilizing the dispersion, tackification, and/or agglomeration of the active compounds, may be used, for example, casein, gelatin, starch, alginic acid, methylcellulose, carboxymethylcellulose, gum arabic, polyvinyl alcohol, turpentine oil, rice bran oil, bentonite, and ligninsulfonates.

For the purpose of improving the flow property of the solid compositions, it is recommendable to use waxes, stearates, or alkyl phosphates.

As peptizers for a dispersible composition, it is also recommendable to use naphthalenesulfonic acid condensation products and polyphosphates.

It is also possible to add a defoamer such as, for example, a silicone oil.

The content of the active ingredient may be adjusted as occasion demands; for the preparation of powdered or granulated products, it is usually 0.5 to 20% by weight, and for the preparation of emulsifiable concentrates or wettable powder products, it is desirably 0.1 to 50% by weight.

For destroying various weeds, inhibiting their growth, or protecting useful plants from the injury caused by weeds, a weed-destroying dosage or a weed growth-inhibiting dosage of the present herbicidal composition is applied as such or after properly diluted with or suspended in water or in other suitable medium, to the soil or the foilage of weeds in the area where the emergence or growth of weeds is undesirable.

The amount of the present herbicide to be used depends on various factors such as, for example, the purpose of application, objective weeds, the emergence or growth state of weeds and crops, the emergence tendency of weeds, weather, environmental conditions, the form of the herbicide composition, the mode of application, the type of the field to be treated, and the time of application.

In applying the present herbicidal composition alone as a selective herbicide, it is suitable to select the dosage of the present active compound from the range of 1 to 500 g per 10 ares. Considering that, in the combined use of herbicides, the optimum dosage thereof is often lower than that in the single use, the present herbicide may be used in an amount lower than the above, when it is used in combination with another sort of herbicide.

The present herbicide is especially valuable for the pre-emergence treatment and initial emergence stage treatment of upland fields and for the early stage and middle stage control of weeds in paddy fields. In order to expand both the range of controllable weed species and the period of time when effective applications are possible or to reduce the dosage, the present herbicides can be used in combination with other herbicides, and this usage is within the scope of this invention. For example, the present herbicide can be used in combination with one or more of the following herbicides: phenoxy fatty acid group herbicides such as 2.4-PA's (e.g., 2,4-dichlorophenoxyacetate), MCP's (e.g., ethyl 2-methyl-4-chlorophenoxyacetate, sodium 2-methyl-4-chlorophenoxyacetate, and ally 2-methyl-4-chlorophenoxyacetate), MCPB (ethyl 2-methyl-4-chlorophenoxybutyrate); diphenyl ether group herbicides such as NITROFEN (2,4-dichlorophenyl 4'-nitrophenyl ether), CNP (2,4,6-trichlorophenyl 4'-nitrophenyl ether), and Chlomethoxynyl (2,4-dichlorophenyl 3'-methoxy-4'-nitrophenyl ether); s-triazine group herbicides such as CAT [2-dichloro-4,6-bis(ethylamino)-s-triazone], Prometryne [2-methylthio-4,6-bis(isopropylamino)-s-triazine], and Simetryne [2-methylthio-4,6-bis(ethylamino)-s-triazine]; carbamate group herbicide such as Molinate (S-ethyl-hexahydro-1H-azepin-1-carbothioate), MCC [methyl N-(3,4-dichlorophenyl) carbamate], IPC [isopropyl N-(3-chlorophenyl) carbamate], Benthiocarb [S-(4-chlorobenzyl)N,N-diethylthiocarbamate]; and other herbicides such as DCPA (3,4-dichloropropionanilide),Butachlor [2-chloro-2', 6'-diethyl-N-(butoxymethyl)-acetanilide], Alachlor [2-chloro-2',6'-diethyl-N-(methoxymethyl)acetanilide], Bentazon [3-isopropyl-2,1,3-benzothiadiazinone-(4)-2,2-dioxide], trifluralin ($\alpha,\alpha,\alpha$-trifluoro-2,6-dinitro-N,N-dipropyl-p-toluidine), and DCMU [3-(3,4-dichlorophenyl)-1,1-dimethylurea]. The above abbreviations conform to the description in "Pesticide Manual, 1978" published by Japan Plant Protection Association.

The following examples illustrate the herbicidal effect, the formulations, and the process of synthesis of the compounds of this invention, but the invention is not to be limited to these examples.

TEST EXAMPLE 1

Controlling effect on paddy field weeds of preemergence state

Pots (1/10,000-are) were filled with soil to simulate a paddy field, and planted with seeds of barnyard grass, monochoria, umbrella plant, and hotarui, and with tubers of arrowhead, respectively, which are all injurious weeds grown in paddy fields, were conditioned so as to be in a pre-emergence stage.

The soil in the pots was treated with each of the present active compounds (listed in Table 1) formulated to a given concentration of liquid, by spraying. After 21 days, the percent control of weed growth compared with that on the untreated plot was evaluated and the herbicidal activity was judged according to the following criterion.

Criterion for judging herbicidal activity

| Degree of herbicidal activity | Percent control of weed growth (%) |
| --- | --- |
| 5 | 100 |
| 4 | 90–99 |
| 3 | 80–89 |
| 2 | 70–79 |
| 1 | <70 |

The results were summarized in Table 2.

TABLE 2

| Compound No. | Amount of active ingredient applied (g/are) | Effect of pre-emergence treatment | | | | |
| --- | --- | --- | --- | --- | --- | --- |
| | | Barnyard grass | Monochoria | Umbrella plant | Hotarui | Arrowhead |
| 1 | 30 | 5 | 5 | 5 | 5 | 5 |
| 2 | 30 | 5 | 5 | 5 | 4 | 5 |
| 3 | 30 | 5 | 5 | 5 | 5 | 5 |
| 5 | 30 | 5 | 5 | 5 | 5 | 5 |
| 6 | 30 | 5 | 5 | 5 | 5 | 5 |
| 7 | 30 | 5 | 5 | 5 | 5 | 5 |
| 8 | 30 | 5 | 5 | 5 | 5 | 5 |
| 9 | 30 | 5 | 5 | 5 | 5 | 5 |

TABLE 2-continued

| Compound No. | Amount of active ingredient applied (g/are) | Effect of pre-emergence treatment | | | | |
| --- | --- | --- | --- | --- | --- | --- |
| | | Barnyard grass | Monochoria | Umbrella plant | Hotarui | Arrowhead |
| 13 | 30 | 5 | 5 | 5 | 5 | 5 |
| 14 | 30 | 5 | 5 | 5 | 5 | 5 |
| 15 | 30 | 5 | 5 | 5 | 5 | 5 |
| 16 | 30 | 5 | 5 | 5 | 5 | 5 |
| 17 | 30 | 5 | 5 | 5 | 5 | 5 |
| 18 | 30 | 5 | 5 | 5 | 5 | 5 |
| 19 | 30 | 5 | 5 | 5 | 5 | 5 |
| 20 | 30 | 5 | 5 | 5 | 5 | 5 |
| 21 | 30 | 5 | 5 | 5 | 5 | 5 |
| 22 | 30 | 5 | 5 | 5 | 5 | 5 |
| 23 | 30 | 5 | 5 | 5 | 4 | 5 |
| 24 | 30 | 5 | 5 | 5 | 4 | 5 |
| 40 | 30 | 5 | 5 | 5 | 5 | 5 |
| 41 | 30 | 5 | 5 | 5 | 5 | 5 |
| 42 | 30 | 5 | 5 | 5 | 5 | 5 |
| 43 | 30 | 5 | 5 | 5 | 5 | 5 |

TEST EXAMPLE 2

Controlling effect on paddy field weeds of post-emergence stage

Pots (1/10,000-are) were filled with soil to simulate a paddy field and grown with each of injurious weeds of the following leaf age. In addition, young seedlings of rice plant (cultivar "Niphonbare") of the 2.5 leaf age were transplanted to the soil on the day before the treatment with each of the present herbicides. After 21 days from the treatment, the herbicidal effect and the degree of crop injury were evaluated by comparing the results with those on the untreated plot.

| Species of sample weed | Leaf age of weed |
| --- | --- |
| Barnyard grass | 1 |
| Monochoria | 2–3 |
| Umbrella plant | 1–2 |
| Hotarui | 2–3 |
| Arrowhead | 3 |

Criterion for judging degree of chemical injury
H: High (including withering)
M: Medium
L: Low
N: None The criterion for judging the herbicidal activity is in accordance with Test Example 1. The results were summerized in Table 3.

TABLE 3

| Compound No. | Amount of active ingredient applied (g/are) | Effect of post-emergence treatment | | | | | Chemical injury paddy rice |
| --- | --- | --- | --- | --- | --- | --- | --- |
| | | Barnyard grass | Monochoria | Umbrella plant | Hotarui | Arrowhead | |
| 1 | 30 | 5 | 5 | 5 | 4 | 5 | L |
| 2 | 30 | 5 | 4 | 4 | 2 | 5 | N |
| 3 | 30 | 5 | 5 | 5 | 4 | 5 | N |
| 5 | 30 | 5 | 5 | 5 | 4 | 4 | L |
| 6 | 30 | 5 | 5 | 5 | 4 | 4 | L |
| 7 | 30 | 5 | 5 | 5 | 4 | 4 | L |
| 8 | 30 | 5 | 5 | 5 | 4 | 4 | L |
| 9 | 30 | 5 | 5 | 5 | 4 | 4 | L |
| 13 | 30 | 5 | 5 | 5 | 4 | 5 | L |
| 14 | 30 | 5 | 5 | 5 | 5 | 5 | L |
| 15 | 30 | 5 | 5 | 5 | 4 | 4 | L |
| 16 | 30 | 5 | 4 | 4 | 3 | 2 | L |
| 17 | 30 | 5 | 4 | 5 | 3 | 2 | N |
| 18 | 30 | 5 | 5 | 5 | 4 | 3 | L |
| 19 | 30 | 5 | 5 | 5 | 5 | 3 | L |

TABLE 3-continued

| Compound No. | Amount of active ingredient applied (g/are) | Effect of post-emergence treatment | | | | | Chemical injury paddy rice |
|---|---|---|---|---|---|---|---|
| | | Barnyard grass | Mono choria | Umbrella plant | Hotarui | Arrowhead | |
| 20 | 30 | 5 | 4 | 5 | 4 | 3 | L |
| 21 | 30 | 5 | 4 | 5 | 3 | 2 | L |
| 22 | 30 | 4 | 4 | 5 | 2 | 2 | N |
| 23 | 30 | 4 | 4 | 4 | 3 | 2 | N |
| 24 | 30 | 3 | 4 | 4 | 3 | 2 | N |
| 40 | 30 | 5 | 5 | 5 | 4 | 4 | L |
| 41 | 30 | 5 | 5 | 5 | 5 | 5 | L |
| 42 | 30 | 5 | 5 | 5 | 4 | 4 | L |
| 43 | 30 | 5 | 5 | 5 | 3 | 3 | L |

TEST EXAMPLE 3

Controlling effect on upland field weeds of pre-emergence stage

Polyethylene vats, 10 cm×20 cm×5 cm (depth), were filled with soil and seeded with oats, barnyard grass, large crabgrass, redroot pigweed, mugwort, Gishi-gishi and umbrella sedge, respectively, and seeds were covered with soil.

The soil was treated with each of the present active compounds formulated to a given concentration of liquid, by spraying. After 21 days, the herbicidal effect was evaluated by comparing the results with those on the untreated plot. The criterion for judging the herbicidal activity is in accordance with Test Example 1. The results were summarized in Table 4.

TEST EXAMPLE 4

Controlling effect on upland field weeds of post-emergence stage

Polyethylene vats, 10 cm×20 cm×5 cm (depth), were filled with soil and seeded with the weeds shown below and soybean seeds, respectively, and the seeds were covered with soil. The weeds and soybean were cultivated respectively to the following leaf ages and then treated with each of the present active compounds at a given dosage.

After 21 days, the herbicidal effect on the weeds and the degree of crop injury to the soybean were evaluated by comparing the results with those on the untreated plot.

| Species of sample plant | Leaf age of sample plant |
|---|---|
| Oats | 2 |
| Large crabgrass | 2 |
| Redroot pigweed | 1 |
| Mugwort | 1 |
| Gishi-gishi | 2 |
| Umbrella sedge | 1 |
| Soybean | First double leaf age |

TABLE 4

| Compound No. | Amount of active ingredient applied (g/are) | Effect of pre-emergence treatment | | | | | | |
|---|---|---|---|---|---|---|---|---|
| | | Oats | Barnyard grass | Large crabgrass | Redroot pigweed | Mugwort | Gishi-gishi | Umbrella sedge |
| 1 | 30 | 4 | 5 | 5 | 5 | 5 | 5 | 5 |
| 2 | 30 | 2 | 5 | 5 | 5 | 5 | 5 | 5 |
| 3 | 30 | 5 | 5 | 5 | 5 | 5 | 5 | 5 |
| 5 | 30 | 5 | 5 | 5 | 5 | 5 | 5 | 5 |
| 6 | 30 | 5 | 5 | 5 | 5 | 5 | 5 | 5 |
| 7 | 30 | 5 | 5 | 5 | 5 | 5 | 5 | 5 |
| 8 | 30 | 5 | 5 | 5 | 5 | 5 | 5 | 5 |
| 9 | 30 | 5 | 5 | 5 | 5 | 5 | 5 | 5 |
| 13 | 30 | 5 | 5 | 5 | 5 | 5 | 5 | 5 |
| 14 | 30 | 5 | 5 | 5 | 5 | 5 | 5 | 5 |
| 15 | 30 | 5 | 5 | 5 | 5 | 5 | 5 | 5 |
| 16 | 30 | 4 | 5 | 5 | 5 | 5 | 5 | 5 |
| 17 | 30 | 2 | 4 | 5 | 5 | 5 | 5 | 5 |
| 18 | 30 | 4 | 5 | 5 | 5 | 5 | 5 | 5 |
| 19 | 30 | 5 | 5 | 5 | 5 | 5 | 5 | 5 |
| 20 | 30 | 5 | 5 | 5 | 5 | 5 | 5 | 5 |
| 21 | 30 | 4 | 5 | 5 | 5 | 5 | 5 | 5 |
| 22 | 30 | 3 | 4 | 4 | 5 | 5 | 5 | 5 |
| 23 | 30 | 2 | 2 | 3 | 5 | 5 | 4 | 5 |
| 24 | 30 | 2 | 3 | 5 | 5 | 4 | 5 | 5 |
| 40 | 30 | 5 | 5 | 5 | 5 | 5 | 5 | 5 |
| 41 | 30 | 5 | 5 | 5 | 5 | 5 | 5 | 5 |
| 42 | 30 | 5 | 5 | 5 | 5 | 5 | 5 | 5 |
| 43 | 30 | 5 | 5 | 5 | 5 | 5 | 5 | 5 |

The criteria for judging the herbicidal activity and chemical injury were in accordance with Test Examples 1 and 2, respectively. The results were summarized in Table 5.

TABLE 5

| Compound No. | Amount of active ingredient applied (g/are) | Effect of post-emergence treatment | | | | | | Chemical injury soybean |
|---|---|---|---|---|---|---|---|---|
| | | Oats | Large crabgrass | Redroot pigweed | Mugwort | Gishi-gishi | Umbrella sedge | |
| 1  | 30 | 2 | 2 | 5 | 5 | 5 | 5 | L |
| 2  | 30 | 2 | 4 | 5 | 5 | 5 | 5 | L |
| 3  | 30 | 3 | 5 | 5 | 5 | 5 | 5 | L |
| 5  | 30 | 5 | 5 | 5 | 5 | 5 | 5 | L |
| 6  | 30 | 5 | 5 | 5 | 5 | 5 | 5 | L |
| 7  | 30 | 5 | 5 | 5 | 5 | 5 | 5 | L |
| 8  | 30 | 5 | 5 | 5 | 5 | 5 | 5 | L |
| 9  | 30 | 5 | 5 | 5 | 5 | 5 | 5 | L |
| 13 | 30 | 5 | 5 | 5 | 5 | 5 | 5 | L |
| 14 | 30 | 5 | 5 | 5 | 5 | 5 | 5 | L |
| 15 | 30 | 5 | 5 | 5 | 5 | 5 | 5 | L |
| 16 | 30 | 2 | 5 | 5 | 5 | 5 | 5 | L |
| 17 | 30 | 2 | 4 | 5 | 5 | 5 | 5 | L |
| 18 | 30 | 3 | 4 | 5 | 5 | 5 | 5 | L |
| 19 | 30 | 5 | 5 | 5 | 5 | 5 | 5 | L |
| 20 | 30 | 5 | 5 | 5 | 5 | 5 | 5 | L |
| 21 | 30 | 2 | 5 | 5 | 5 | 5 | 5 | L |
| 22 | 30 | 2 | 5 | 5 | 5 | 5 | 5 | L |
| 23 | 30 | 2 | 4 | 5 | 4 | 4 | 5 | L |
| 24 | 30 | 2 | 3 | 5 | 5 | 5 | 5 | L |
| 40 | 30 | 5 | 5 | 5 | 5 | 5 | 5 | L |
| 41 | 30 | 5 | 5 | 5 | 5 | 5 | 5 | L |
| 42 | 30 | 5 | 5 | 5 | 5 | 5 | 5 | L |
| 43 | 30 | 5 | 5 | 5 | 5 | 5 | 5 | L |

EXAMPLE 1

A wettable powder composition obtained by uniformly mixing and grinding the following constituents:

| Compund No. 2 | 50 parts |
|---|---|
| Mixture of clay and white carbon (clay is major consitiuent) | 45 parts |
| Polyoxyethylene nonylphenyl ether | 5 parts |

EXAMPLE 2

A granule composition obtained by uniformly mixing and grinding the following constituents, kneading the mixture with a suitable amount of water, and granulating the kneaded mixture:

| Compound No. 13 | 5 parts |
|---|---|
| Mixture of bentonite and clay | 90 parts |
| Calcium liguninsulfonate | 5 parts |

EXAMPLE 3

An emulsifiable concentrate obtained by uniformly mixing the following constituents:

| Compound No. 15 | 50 parts |
|---|---|
| Xylene | 40 parts |
| Mixture of polyoxyethylene nonylphenyl ether and calcium alkylbenzenesulfonate | 10 parts |

Synthetic Process Example 1

Synthesis of 1-(2,4-dichloro-5-isopropoxyphenyl)-3-methyl-4-difluoromethyl-$\Delta^2$-1,2,4-triazolin-5-one.

To 60 ml of cyclohexane were added 2 g (0.0066 mole) of 1-(2,4-dichloro-5-isooropoxyphenyl)-3-methyl-$\Delta^2$-1,2,4-triazolin-5-one, 2 g of tetrabutylammonium bromide and 2 g of caustic soda to obtain a suspension to which 2 g (0.023 mole) of chlorodifluoromethane was introduced over a period of one hour while refluxed, to complete the reaction, and cooled to room temperature. The reaction mixture was added with 100 ml water and subjected to extraction with diethyl ether.

An organic layer formed was taken and washed successively with aqueous caustic soda, water, diluent aqueous hydrogen chloride and water, dried over anhydrous sodium sulfate and distilled to remove the organic solvents. There was obtained 1.06 g of oily product.

The oily product was allowed to stand at room temperature and recrystallized from n-hexane, whereby the intended product was obtained; m.p. 81.3° C., yield 41.0%.

Synthetic Process Example 2

Synthesis of 1-(2,4-dichloro-5-propargyloxyphenyl)-3-methyl-4-propargyl-$\Delta^2$-1,2,4-triazolin-5-one.

To 30 ml of acetone were added 0.5 g of 1-(2,4-dichloro-5-propargyloxyphenyl)-3-methyl-$\Delta^2$-1,2,4-triazolin-5-one, 1 g of potassium carbonate, and 0.5 g of propargyl bromide. The mixture was refluxed for 2 hours and cooled to room temperature. After the excess of potassium carbonate and potassium bromide formed was filtered off, the filtrate distilled to remove acetone.

The resulting crystal was recrystallized from ethyl acetate-n-hexane (1:5), whereby the intended product was obtained; m.p. 140.6° C., yield 80.4%.

Synthetic Process Example 3

Synthesis of
1-(2,4-dichloro-5-propargyloxyphenyl)-3-methyl-4-difluoromethyl-$\Delta^2$-1,2,4-triazolin-5-one.

To 30 ml of acetone were added 0.54 g of 1-(2,4-dichloro-5-hydroxyphenyl)-3-methyl-4-difluoromethyl-$\Delta^2$-1,2,4-triazolin-5-one, 1 g of potassium carbonate, and 0.5 g of propargyl bromide. The mixture was refluxed for 2 hours, and cooled to room temperature. After the excess of potassium carbonate and potassium bromide formed was filtered off, the reaction mixture was subjected to distillation to remove acetone.

The resulting crystal was recrystallized from n-hexane, whereby 0.59 g of the intended product was obtained;

m.p. 114.4° C., yield 98.3%.

Synthetic Process Example 4

Synthesis of
1-(2,4-dichloro-5-isopropoxyphenyl)-3-methyl-4-(1,1,2,2-tetrafluoroethyl)-$\Delta^2$-1,2,4-triazolin-5-one.

In 60 ml of dimethylformamide were dissolved 3.02 g (0.01 mol) of 1-(2,4-dichloro-5-isopropoxyphenyl)-3-methyl-$\Delta^2$-1,2,4-triazolin-5-one, and 0.40 g (0.01 mol) of caustic soda powder was added to the solution.

The mixture was heated at 50°–60° C., and the excess of tetrafluoroethylene gas was introduced thereinto. The gas had been produced by adding dropwise a solution of 20 g of 1,2-dibromo-1,1,2,2-tetrafluoroethane in 20 ml of methanol to a suspension of 16.25 g of zink fine powder in 120 ml of methanol.

The reaction mixture was poured into ice-water, extracted with diethyl ether, washed twice with 10% aqueous sodium chloride solution and with water and then saturated sodium chloride solution, and dried over anhydrous magnesium sulfate.

After solvent was freed by distillation, the residue was recrystallized from diethyl ether—petroleum ether (1:5), whereby 1.47 g of the intended product was obtained;

m.p. 102–103.5° C., yield 36.5%.

Synthetic Process Examples 5

Synthesis of
1-[2,4-dichloro-5-(1,1,2,2-tetrafluoroethoxy)phenyl]-3-methyl-4-(1,1,2,2-tetrafluoroethyl)-$\Delta^2$-1,2,4-triazolin-5-one.

In 30 ml of dimethylformamide was suspended 0.78 g (0.003 mol) of 1-(2,4-dichloro-5-hydroxyphenyl)-3-methyl-$\Delta^2$-1,2,4-triazolin-5-one. The suspension was added with 0.25 g of caustic soda and heated at 50–60° C.

Into the mixture was introduced the excess of tetrafluoroethylene gas which had been produced in the same way as in Synthetic Process Example 4.

The resulting product was poured into ice-water, extracted with diethyl ether, whereby 0.33 g of the intended oily product was obtained;

$n_D^{15.0}$ 1.4840, yield 23.9%.

Synthetic Process Example 6

Synthesis of
1-(2,4-dichloro-5-hydroxyphenyl)-3-methyl-4-difluoromethyl-$\Delta^2$-1,2,4-triazolin-5-one.

A mixture of 6 g (0.017 mol) of 1-(2,4-dichloro-5-isopropoxyphenyl)-3-methyl-4-difluoromethyl-$\Delta^2$-1,2,4-triazolin-5-one, 60 ml of 47% hydrobromic acid, and 150 ml of acetic acid were refluxed for 4 hours.

After cooled, acetic acid was removed by distillation.

The resulting product was poured into 150 ml of ice-water, filtered, whereby 5.03 g of the intended crystal product was obtained;

m.p. 175.3° C., yield 95.3%.

Synthetic Process Example 7

Synthesis of
1-(2,4-dichloro-5-propargyloxyphenyl)-3-methyl-$\Delta^2$-1,2,4-triazolin-5-one.

In 20 ml of xylene were dissolved 1.45 g (0.0062 mol) of 2,4-dichloro-5-propargyloxyphenyl hydrazine and 1.2 g (0.007 mol) of ethyl N-(1-ethylthioethylidene carbamate. The solution was heated at 80° C. for 30 minutes, and cooled at room temperature.

Triethylamine was added thereto, and the mixture was refluxed for 2 hours. After the reaction mixture was cooled to room temperature, crystals formed were collected;

m.p. 229.1° C., yield 80.6%.

Synthetic Process Example 8

Synthesis of
1-(2,4-dichloro-5-propargyloxyphenyl)-3-isopropyl-$\Delta^2$-1,2,4-triazolin-5-one.

The procedures of Synthetic Process Example 7 were repeated, provided that in place of 1.2 g of ethyl N-(1-ethylthioethylidene)carbamate 1.3 g (0.007 mol) of ethyl N-(1-ethoxyisobutylidene)carbamate was used. There was obtained 1-(2,4-dichloro-5-propargyloxyphenyl)-3-isopropyl-$\Delta^2$-1,2,4-triazolin-5-one;

m.p., 162.9° C., yield 80.1%.

What is claimed is:

1. A $\Delta^2$-1,2,4-triazoline-5-one derivative represented by the formula (I)

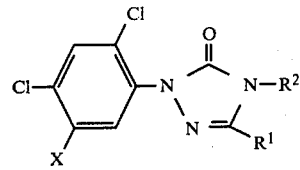

wherein $R^1$ is a $C_1$–$C_4$ alkyl group; $R^2$ is a $C_3$–$C_5$ alkynyl group, a halomethyl group, or a haloethyl group; and X is a $C_1$–$C_4$ alkoxy group, a $C_2$–$C_6$ alkenyloxy group, a $C_2$–$C_6$ alkoxyalkoxy group, a $C_3$–$C_8$ alkynyloxy group, a hydroxy group, a halomethyloxy group, a 3-chloro-2-propenoxy group, a 1-ethynyl-1-cyclohexyloxy group, or a halethyloxy group.

2. A $\Delta^2$-1,2,4-triazolin-5-one derivative of claim 1, wherein $R^2$ is the halomethyl group.

3. A $\Delta^2$-1,2,4-triazolin-5-one derivative of claim 2, wherein the halomethyl group is a difluoromethyl group.

4. A $\Delta^2$-1,2,4-triazolin-5-one derivative of claim 1, wherein X is a $C_1$–$C_4$ alkoxy group, a $C_2$–$C_6$ alkenyloxy group, a $C_2$–$C_6$ alkoxyalkoxy group, a 3-chloro-2-propenoxy group, a 1-ethynyl-1-cyclohexyloxy group, or a $C_3$–$C_8$ alkynyloxy group.

5. A $\Delta^2$-1,2,4-triazolin-5-one derivative of claim 1, wherein $R^2$ is a halomethyl group; and X is a $C_1$–$C_4$ alkoxy group, a $C_2$–$C_6$ alkenyloxy group, a 3-chloro-2- propenoxy group, a 1-ethynyl-1-cyclohexyloxy group, a $C_2$–$C_6$ alkoxyalkoxy group, or a $C_3$–$C_8$ alkynyloxy group.

6. A $\Delta^2$-1,2,4-triazolin-5-one derivative of claim 5, wherein the halomethyl group is a diflouromethyl group.

7. 1(2,4-dichloro-5-isopropoxyphenyl)-3-methyl-4-difluromethyl-$\Delta^2$-1,2,4-triazolin-5one.

8. 1-(2,4-dichloro-5-allyloxyphenyl)-3-methyl-4-difluromethyl-$\Delta^2$-1,2,4-triazolin-5-one.

9. 1-(2,4-dichloro-5-propargyloxyphenyl)-3-methyl-4-difluromethyl-$\Delta^2$-1,2,4-triazolin-5-one.

10. 1-(2,4-dichloro-5-methoxymethoxyphenyl)-3-methyl-4-difluoromethyl-$\Delta^2$-1,2,4-triazolin-5-one.

11. A herbicidal composition comprising an effective amount of a $\Delta^2$-1,2,4-triazolin-5-one derivative and a diluent, said derivative being represented by the formula

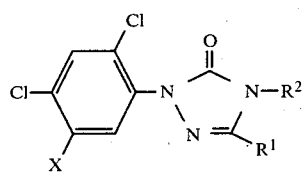

(I)

wherein $R^1$ is a $C_1$–$C_4$ alkyl group; $R^2$ is a $C_3$–$C_5$ alkynyl group, a halomethyl group, or a haloethyl group; and X is $C_1$–$C_4$ alkoxy group, a $C_2$–$C_6$ alkenyloxy group, a $C_2$–$C_6$ alkoxyalkoxy group, a $C_3$–$C_8$ alkynyloxy group, a hydroxy group, a halomethyloxy group, a 3-chloro-2-propenoxy group, a 1-ethynyl-1-cyclohexyloxy group, or a haloethyloxy group.

12. A herbidical composition of claim 11, wherein $R^2$ is a halomethyl group.

13. A herbidical composition of claim 12, wherein the halomethyl group is a difluoromethyl group.

14. A herbicidal composition of claim 11, wherein X is a $C_1$–$C_4$ alkoxy group, a $C_2$–$C_6$ alkenyloxy group, a $C_2$–$C_6$ alkoxyalkoxy group, a 3-chloro-2-propenoxy group, a 1-ethynyl-1-cyclohexyloxy group, or a $C_3$–$C_8$ alkynyloxy group.

15. A herbicidal composition of claim 11, wherein $R^2$ is a halomethyl group; and X is a $C_1$–$C_4$ alkoxy group, a $C_2$–$C_6$ alkenyloxy group, a $C_2$–$C_6$ alkoxyalkoxy group, a 3-chloro-2-propenoxy group, a 1-ethynyl-1-cyclohexyloxy group, or a $C_3$–$C_8$ alkynyloxy group.

16. A herbicidal composition of claim 15, wherein the halomethyl group is a difluoromethyl group.

17. A herbicidal composition of claim 11, wherein the $\Delta^2$-1,2,4-triazolin-5-one derivative is 1-(2,4-dichloro-5-isopropoxyphenyl)-3-methyl-4-difluromethyl-$\Delta^2$-1,2,4-triazolin-5-one.

18. A herbicidal composition of claim 11, wherein the $\Delta^2$-1,2,4-triazolin-5-one derivative is 1-(2,4-dichloro-5-allyloxyphenyl)-3-methyl-4-difluoromethyl-$\Delta^2$-1,2,4-triazolin-5-one.

19. A herbicidal composition of claim 11, wherein the $\Delta^2$-1,2,4-triazolin-5-one derivative is 1-(2,4-dichloro-5-propargyloxyphenyl)-3-methyl-4-difluoromethyl-$\Delta^2$-1,2,4-triazolin-5-one.

20. A herbicidal composition of claim 11, wherein the $\Delta^2$-1,2,4-triazolin-5-one derivative is 1-(2,4-dichloro-5-methoxymethoxyphenyl)-3-methyl-4-difluoromethyl-$\Delta^2$-1,2,4-triazolin-5-one.

21. A method of killing plants comprising applying to the plants a herbicidally effective amount of a compound according to claim 1.

22. A method of killing plants comprising applying to the plants a herbicidally effective amount of a compound according to claim 2.

23. A method of killing plants comprising applying to the plants a herbicidally effective amount of a compound according to claim 3.

24. A method of killing plants comprising applying to the plants a herbicidally effective amount of a compound according to claim 4.

25. A method of killing plants comprising applying to the plants a herbicidally effective amount of a compound according to claim 5.

26. A method of killing plants comprising applying to the plants a herbicidally effective amount of the compound of claim 6.

27. A method of killing plants comprising applying to the plants a herbicidally effective amount of the compound of claim 7.

28. A method of killing plants comprising applying to the plants a herbicidally effective amount of the compound of claim 8.

29. A method of killing plants comprising applying to the plants a herbicidally effective amount of the compound of claim 9.

30. A method of killing plants comprising applying to the plants a herbicidally effective amount of the compound of claim 10.

31. A method according to claim 21 wherein the compound is applied before emergence of the plants.

32. A method according to claim 21 wherein the compound is applied after emergence of the plants.

33. A method of selectively killing weeds in a crop of useful plants comprising applying to the crop an amount of a compound of claim 1 effective to kill the weeds but insufficient to kill the useful crop.

34. A method according to claim 33 wherein the herbicide is applied efore emergence of the plants.

35. A method according to claim 34 wherein the crop is rice.

36. A method according to claim 33 wherein the herbicide is applied after emergence of the plants.

37. A method according to claim 36 wherein the crop is rice or soybeans.

38. A compound according to claim 5 wherein X is 1-ethynyl-1-cyclohexyloxy.

* * * * *

UNITED STATES PATENT AND TRADEMARK OFFICE
CERTIFICATE OF CORRECTION

PATENT NO. : 4,398,943
DATED : August 16, 1983
INVENTOR(S) : KAJIOKA ET AL

It is certified that error appears in the above-identified patent and that said Letters Patent is hereby corrected as shown below:

IN THE ASSIGNEE:

Change "Nikon" to --Nihon--.

Signed and Sealed this

Seventeenth Day of April 1984

[SEAL]

Attest:

GERALD J. MOSSINGHOFF

Attesting Officer

Commissioner of Patents and Trademarks